United States Patent [19]

Thomas et al.

[11] Patent Number: 5,552,306

[45] Date of Patent: Sep. 3, 1996

[54] PRODUCTION OF γ-LINOLENIC ACID BY A Δ6-DESATURASE

[75] Inventors: Terry L. Thomas, College Station; Avutu S. Reddy, Bryan; Michael Nuccio, College Station, all of Tex.; Georges L. Freyssinet, Saint Cyr au Mont d'Or, France

[73] Assignee: Rhone-Poulenc Agrochimie, Lyons, France

[21] Appl. No.: 307,382

[22] Filed: Sep. 14, 1994

Related U.S. Application Data

[63] Continuation of Ser. No. 959,952, Oct. 13, 1992, abandoned, which is a continuation of Ser. No. 817,919, Jan. 8, 1992, abandoned, which is a continuation-in-part of Ser. No. 774,475, Oct. 10, 1991, abandoned.

[51] Int. Cl.$^6$ .............................. C12P 7/64; C12N 15/63; C12N 9/02; C12N 5/14
[52] U.S. Cl. ...................... 435/134; 435/170; 435/320.1; 435/252.3; 435/243; 435/240.4; 435/172.3; 435/69.1; 435/70.1; 435/71.2; 435/189; 536/23.2; 536/23.7; 530/825
[58] Field of Search ........................ 800/205; 435/172.3, 435/520.1, 134, 170, 240.4, 243, 252.3, 189, 69.1, 70.1, 71.2; 536/23.2, 23.7; 530/825

[56] References Cited

U.S. PATENT DOCUMENTS 4,736,866  4/1988  Leder et al. .................................. 800/1

FOREIGN PATENT DOCUMENTS 0255378  2/1988  European Pat. Off. ........ C12N 15/00
9010076  9/1990  WIPO ............................ C12N 15/82

OTHER PUBLICATIONS

M. Harpsoer et al. Mol. Gen. Genet., vol. 212 ('88) pp. 182–190.
D. Murphy, Biochem. Soc. Transamerican, vol. 17, (1989) pp. 685–686.
D. Ow et al., PNAS, vol. 84 (Jul. 1987) pp. 4870–4874.
C. Somerville et al. Science, vol. 252 (5 Apr. '91) pp. 80–87.
L. M. Hoffman et al. Plant Mol. Biol, vol. 11 #17 ('88) pp. 717–729.
B. Larkins et al. (Abstract) J. Cell. Biochem., Suppl. O (9, part C) ('85) p. 264.
T. Ohtani et al. Plant Molecular Biology, vol. 16 ('91) pp. 117–128.
Wada et al. Plant Cell Physiol. (Tokyo) vol. 30 #7 ('89) pp. 971–978.
Stymne, S., et al. Biochem. J., vol. 240 (1986) pp. 385–393.
Wada, H., et al. Nature, vol. 347 (1990) pp. 200–203.
Bafor (1990) "Properties of the Glycerol Acylating Enzymes in Microsomal Preparations from the Developing Seeds of Safflower (*Carthamus tinctorius*) and Turnip Rape (*Brassica campestris*) and their Ability to Assembles Cocoa–Butter Type Fats," *Journal of the American Oil Chemists Society* 67:217.

Ohlrogge, J. B., Browse, J., and Somerville, C. R. (1991) *Biochim. Biophys. Acta* 1082:1–26.
Sugano, et al. (1986) "Effects of Mold Oil Containing γ-Linolenic Acid on the Blood Cholesterol and Eicosanoid Levels in Rats" *Agric. Biol. Chem.* 50, 2483–2491.
Crozier, et al. (1989) "Black Currant Seed Oil Feeding and Fatty Acid in Liver Lipid Classes of Guinea Pigs" *Lipids* 24, 460–466.
Brenner (1976) "Regulatory Function of Δ–Desaturase—A Key Enzyme of Polyunsaturated Fatty Acid Synthesis" *Adv. Exp. Med. Biol.* 83, 85–101.
Stumpf (1987) "Plant Lipid Biotechnology Through the Looking Glass" *J. American Oil Chemical Society* 64, 1641–1645.
Kenyon (1972) "Fatty Acid Composition of Unicellular Strains of Blue Green Algae" *J. Bacteriology* 109, 827–834.
Kenyon, et al. (1972) "Fatty Acid Composition and Physiological Properties of Some Filamentous Blue–Green Algae" *Arch. Mikrobiol.* 83, 216–236.
Murata (1989) "Low–Temperature Effects on Cyanobacterial Membranes" *Journal of Bioenergetics and Biomembranes* 21, 60–75.
Murata, et al. (1987) "Lipids of Blue Green Algae ( Cyanobacteria) In: Stumpf PK (eds) The Biochemistry of Plants" *Academic Press, Orlando, FL* 9, 315–347.
Dahmer, et al. (1989) "A Rapid Screening Technique for Determining the Lipid Composition of Soybean Seed" *J. Amer. Oil Chem. Soc.* 66, 543–548.
Devereux, et al. (1984) "A Comprehensive Set of Sequence Analysis Programs for the VAX" *Nucleic Acids Res.* 12, 387–395.
Kyte, et al. (1982) "A Simple Method for Dosplaying the Hydropathic Character of a Protein" *J. Mol. Biol.* 157, 105–132.
Sanger, et al. (1977) "DNA Sequencing with Chain–Terminating Inhibitors" *Proc. Natl. Acad. Sci. USA* 74, 5463–5467.
Wada, et al. (1990) "Enhancement of Chilling Tolerance of a Cyanobacterium by Genetic Manipulation of Fatty Acid Desaturation" *Nature* 374, 200–203. 2491.
Stymne, et al. (1986) "Biosynthesis of γ–Linolenic Acid in Cotyledons and Micro–Somal Preparations of the Developing Seeds of Common Borage (*Borago officinalis*)" *Biochem. J.* 240, 385–393.

(List continued on next page.)

Primary Examiner—Charles C. P. Rories
Attorney, Agent, or Firm—Scully, Scott, Murphy & Presser

[57] ABSTRACT

Linoleic acid is converted into γ-linolenic acid by the enzyme Δ6-desaturase. The present invention is directed to an isolated nucleic acid comprising the Δ6-desaturase gene. More particularly, the isolated nucleic acid comprises the promoter, coding region and termination regions of the Δ6-desaturase gene. The present invention provides recombinant constructions comprising the Δ6-desaturase coding region in functional combination with heterologous regulatory sequences. The nucleic acids and recombinant constructions of the instant invention are useful in the production of GLA in transgenic organisms.

23 Claims, 3 Drawing Sheets

OTHER PUBLICATIONS

Weete, J. D. (1980) *Lipid Biochemistry of Fungi and Other Organisms,* Plenum Press, New York, Chapter 6, 157–163.

Horrobin, et al. (1984) "Effects of Essential Fatty Acids on Prostaglandin Biosynthesis" *Biomed. Biochim. Acta* 43, S114–S120.

Aebersold et al., (1987) "Internal amino acid sequence analysis of proteins separated by one or two-dimensional gel electrophoresis after in situ protease digestion on nitrocellulose," Proc. Natl. Acad. Sci. USA 84: 6970–6974.

Jaye et al., (1983) "Isolation of a human anti-haemophilic factor IX cDNA clone using a unique 52-base synthetic oligonucleotide probe deduced from the amino acid sequence of bovine factor IX," Nucleic Acids Research 11(8): 2325–2335.

Miguel et al., "Arabidopsis Mutants Deficient in Polyunsaturated Fatty Acid Synthesis," Jan. 1992, *J. Biol. Chem.* 267: 1502–1509.

Shanklin et al., "Stearoyl–acyl–carrier–protein Desaturase from Higher Plants is Structurally Unrelated to the Animal and Fungal Homologs," Mar. 1991, *Proc. Natl. Acad. Sci., USA* 88: 2510–2514.

Yadav et al., "Cloning of Higher Plant ω–3 Fatty Acid Desaturases," 1993, *Plant Physiology* 103: 467–476.

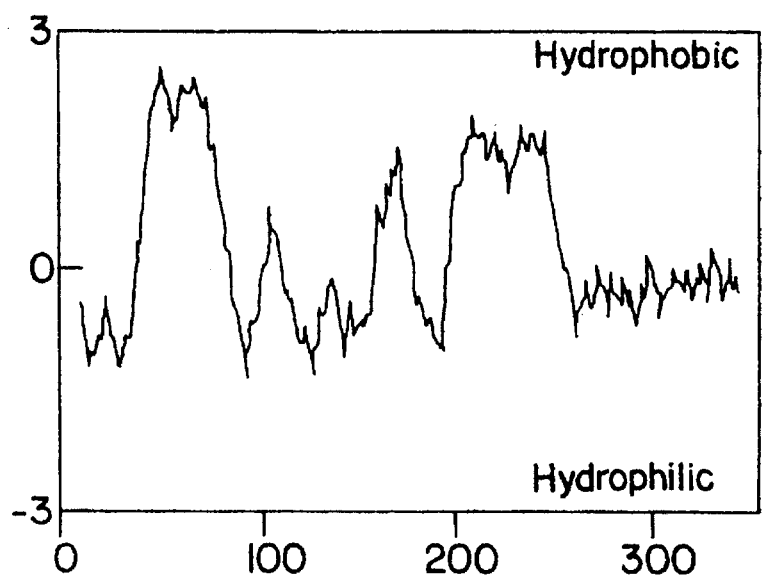
FIG. IA
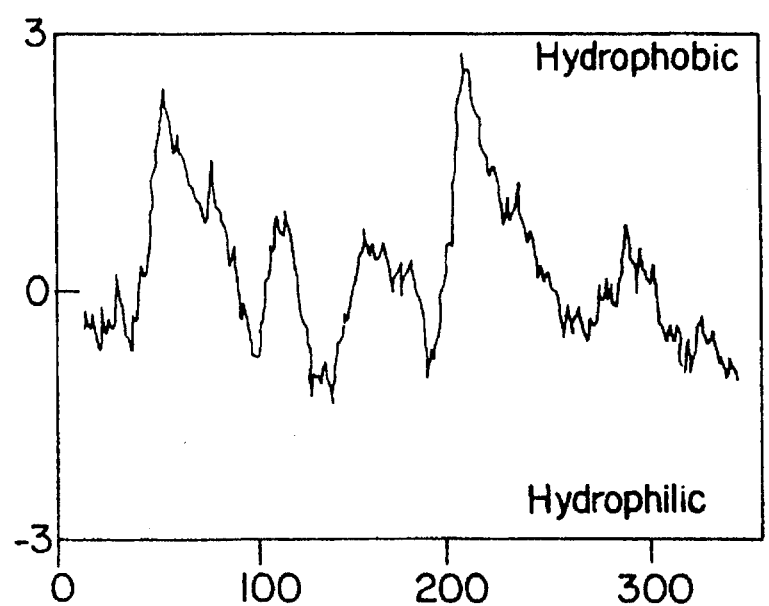
FIG. IB

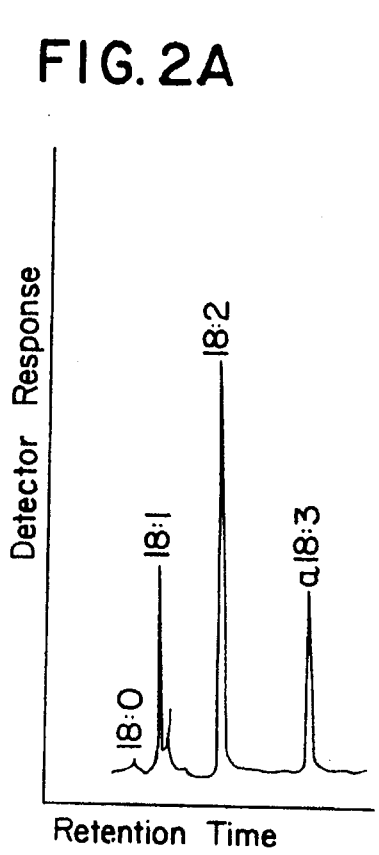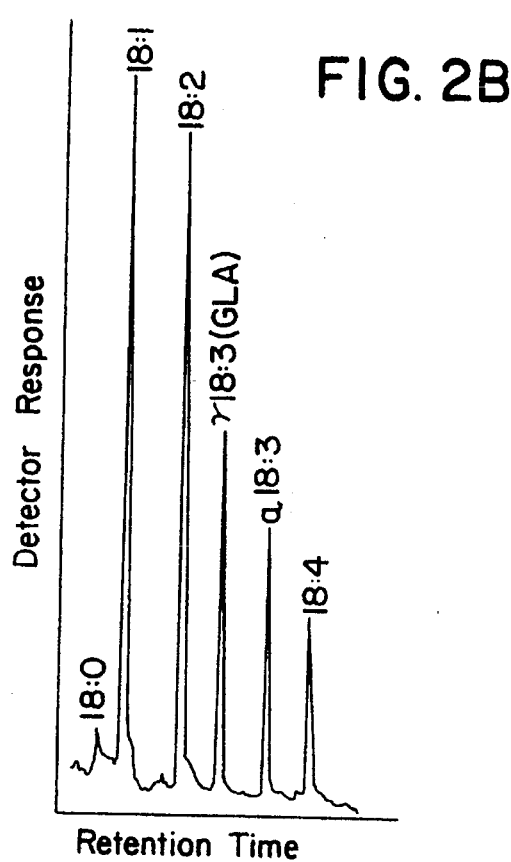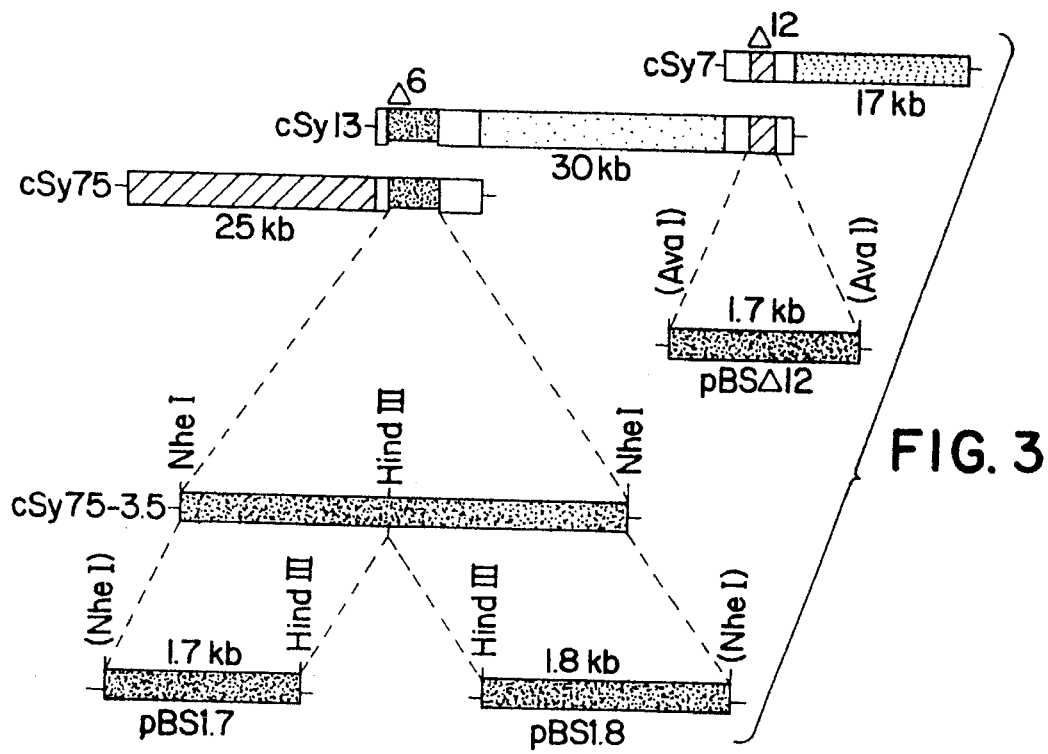

ns
PRODUCTION OF γ-LINOLENIC ACID BY A Δ6-DESATURASE

This is a continuation of application Ser. No. 07/959,952 filed on Oct. 13, 1992, now abandoned, which is a continuation of Ser. No. 07/817,919 filed on Jan. 8, 1992, now abandoned, which is a continuation-in-part of Ser. No. 07/774,475 filed Oct. 10, 1991, now abandoned.

FIELD OF THE INVENTION

Linoleic acid (18:2) (LA) is transformed into gamma linolenic acid (18:3) (GLA) by the enzyme Δ6-desaturase. When this enzyme, or the nucleic acid encoding it, is transferred into LA-producing cells, GLA is produced. The present invention provides a nucleic acid comprising the Δ6-desaturase gene. More specifically, the nucleic acid comprises the promoter, coding region and termination regions of the Δ6-desaturase gene. The present invention is further directed to recombinant constructions comprising a Δ6-desaturase coding region in functional combination with heterologous regulatory sequences. The nucleic acids and recombinant constructions of the instant invention are useful in the production of GLA in transgenic organisms.

BACKGROUND OF THE INVENTION

Unsaturated fatty acids such as linoleic ($C_{18}\Delta^{9,12}$) and α-linolenic ($C_{18}\Delta^{9,12,15}$) acids are essential dietary constituents that cannot be synthesized by vertebrates since vertebrate cells can introduce double bonds at the $\Delta^9$ position of fatty acids but cannot introduce additional double bonds between the $\Delta^9$ double bond and the methyl-terminus of the fatty acid chain. Because they are precursors of other products, linoleic and α-linolenic acids are essential fatty acids, and are usually obtained from plant sources. Linoleic acid can be converted by mammals into γ-linolenic acid (GLA, $C_{18}\Delta^{6,9,12}$) which can in turn be converted to arachidonic acid (20:4), a critically important fatty acid since it is an essential precursor of most prostaglandins.

The dietary provision of linoleic acid, by virtue of its resulting conversion to GLA and arachidonic acid, satisfies the dietary need for GLA and arachidonic acid. However, a relationship has been demonstrated between consumption of saturated fats and health risks such as hypercholesterolemia, atherosclerosis and other chemical disorders which correlate with susceptibility to coronary disease, while the consumption of unsaturated fats has been associated with decreased blood cholesterol concentration and reduced risk of atherosclerosis. The therapeutic benefits of dietary GLA may result from GLA being a precursor to arachidonic acid and thus subsequently contributing to prostaglandin synthesis. Accordingly, consumption of the more unsaturated GLA, rather than linoleic acid, has potential health benefits. However, GLA is not present in virtually any commercially grown crop plant.

Linoleic acid is converted into GLA by the enzyme Δ6-desaturase. Δ6-desaturase, an enzyme of about 359 amino acids, has a membrane-bound domain and an active site for desaturation of fatty acids. When this enzyme is transferred into cells which endogenously produce linoleic acid but not GLA, GLA is produced. The present invention, by providing the gene encoding Δ6-desaturase, allows the production of transgenic organisms which contain functional Δ6-desaturase and which produce GLA. In addition to allowing production of large amounts of GLA, the present invention provides new dietary sources of GLA.

SUMMARY OF THE INVENTION

The present invention is directed to an isolated Δ6-desaturase gene. Specifically, the isolated gene comprises the Δ6-desaturase promoter, coding region, and termination region.

The present invention is further directed to expression vectors comprising the Δ6-desaturase promoter, coding region and termination region.

Yet another aspect of this invention is directed to expression vectors comprising a Δ6-desaturase coding region in functional combination with heterologous regulatory regions, i.e. elements not derived from the Δ6-desaturase gene.

Cells and organisms comprising the vectors of the present invention, and progeny of such organisms, are also provided by the present invention.

A further aspect of the present invention provides isolated bacterial Δ6-desaturase.

Yet another aspect of this invention provides a method for producing plants with increased gamma linolenic acid content.

A method for producing chilling tolerant plants is also provided by the present invention.

BRIEF DESCRIPTION OF THE DRAWINGS

FIGS. 1A–1B depicts the hydropathy profiles of the deduced amino acid sequences of *Synechocystis* Δ6-desaturase (Panel 1A) and Δ12-desaturase (Panel 1B). Putative membrane spanning regions are indicated by solid bars. Hydrophobic index was calculated for a window size of 19 amino acid residues [Kyle, et al. (1982) J. Molec. Biol. 157].

FIGS. 2A–2B provides gas liquid chromatography profiles of wild type (Panel 2A) and transgenic (Panel 2B) *Anabaena*.

FIG. 3 is a diagram of maps of cosmid csy75, cSy13 and cSy7 with overlapping regions and subclones. The origins of subclones of csy75, csy75–3.5 and cSy7 are indicated by the dashed diagonal lines. Restriction sites that have been inactivated are in parentheses.

DETAILED DESCRIPTION OF THE INVENTION

Figure 4A:
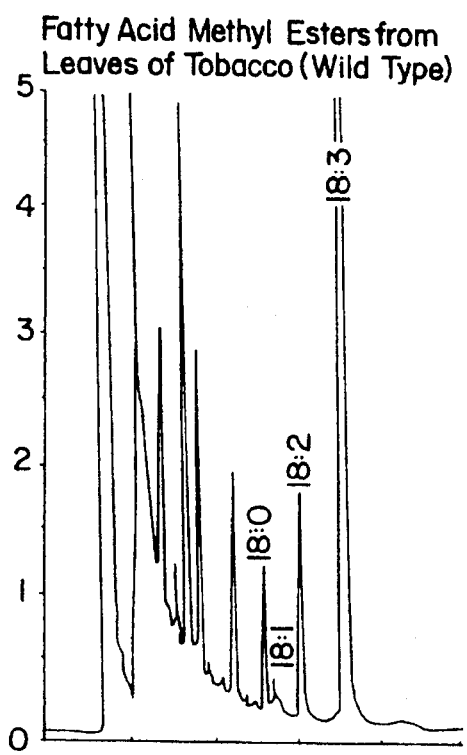
FIGS. 4A–4B provides gas liquid chromatography profiles of wild type (Panel 4A) and transgenic (Panel 4B) tobacco.

The present invention provides an isolated nucleic acid encoding Δ6-desaturase. To identify a nucleic acid encoding Δ6-desaturase, DNA is isolated from an organism which produces GLA. Said organism can be, for example, an animal cell, certain fungi (e.g. *Mortierella*), certain bacteria (e.g. *Synechocystis*) or certain plants (borage, Oenothera, currants). The isolation of genomic DNA can be accomplished by a variety of methods well-known to one of ordinary skill in the art, as exemplified by Sambrook et al. (1989) in *Molecular Cloning: A Laboratory Manual*, Cold Spring Harbor, N.Y. The isolated DNA is fragmented by physical methods or enzymatic digestion and cloned into an appropriate vector, e.g. a bacteriophage or cosmid vector, by any of a variety of well-known methods which can be found in references such as Sambrook et al. (1989). Expression vectors containing the DNA of the present invention are specifically contemplated herein. DNA encoding Δ6-desaturase can be identified by gain of function analysis. The vector containing fragmented DNA is transferred, for example by infection, transconjugation, transfection, into a host organism that produces linoleic acid but not GLA. As used herein, "transformation" refers generally to the incorporation of foreign DNA into a host cell. Methods for introducing recombinant DNA into a host organism are known to one of ordinary skill in the art and can be found, for example, in Sambrook et al. (1989). Production of GLA by these organisms (i.e., gain of function) is assayed, for example by gas chromatography or other methods known to the ordinarily skilled artisan. Organisms which are induced to produce GLA, i.e. have gained function by the introduction of the vector, are identified as expressing DNA encoding Δ6-desaturase, and said DNA is recovered from the organisms. The recovered DNA can again be fragmented, cloned with expression vectors, and functionally assessed by the above procedures to define with more particularity the DNA encoding Δ6-desaturase.

As an example of the present invention, random DNA is isolated from the cyanobacteria *Synechocystis* Pasteur Culture Collection (PCC) 6803, American Type Culture Collection (ATCC) 27184, cloned into a cosmid vector, and introduced by transconjugation into the GLAd-deficient cyanobacterium *Anabaena* strain PCC 7120, ATCC 27893. Production of GLA from *Anabaena* linoleic acid is monitored by gas chromatography and the corresponding DNA fragment is isolated.

The isolated DNA is sequenced by methods wellknown to one of ordinary skill in the art as found, for example, in Sambrook et al. (1989).

In accordance with the present invention, a DNA comprising a Δ6-desaturase gene has been isolated. More particularly, a 3.588 kilobase (kb) DNA comprising a Δ6-desaturase gene has been isolated from the cyanobacteria *Synechocystis*. The nucleotide sequence of the 3.588 kb DNA was determined and is shown in SEQ ID NO:1. Open reading frames defining potential coding regions are present from nucleotide 317 to 1507 and from nucleotide 2002 to 3081. To define the nucleotides responsible for encoding Δ6-desaturase, the 3.588 kb fragment that confers Δ6-desaturase activity is cleaved into two subfragments, each of which contains only one open reading frame. Fragment ORF1 contains nucleotides 1 through 1704, while fragment ORF2 contains nucleotides 1705 through 3588. Each fragment is subcloned in both forward and reverse orientations into a conjugal expression vector (AM542, Wolk et al. [1984] *Proc. Natl. Acad. Sci. USA* 81, 1561) that contains a cyanobacterial carboxylase promoter. The resulting constructs (i.e. ORF1(F), ORF1(R), ORF2(F) and ORF2(R)] are conjugated to wild-type *Anabaena* PCC 7120 by standard methods (see, for example, Wolk et al. (1984) *Proc. Natl. Acad. Sci. USA* 81, 1561). Conjugated cells of *Anabaena* are identified as Neo$^R$ green colonies on a brown background of dying non-conjugated cells after two weeks of growth on selective media (standard mineral media BG11N+ containing 30 μg/ml of neomycin according to Rippka et al., (1979) *J. Gen Microbiol.* 111, 1). The green colonies are selected and grown in selective liquid media (BG11N+ with 15 μg/ml neomycin). Lipids are extracted by standard methods (e.g. Dahmer et al., (1989) *Journal of American Oil Chemical Society* 66, 543) from the resulting transconjugants containing the forward and reverse oriented ORF1 and ORF2 constructs. For comparison, lipids are also extracted from wild-type cultures of *Anabaena* and *Synechocystis*. The fatty acid methyl esters are analyzed by gas liquid chromatography (GLC), for example with a Tracor-560 gas liquid chromatograph equipped with a hydrogen flame ionization detector and a capillary column. The results of GLC analysis are shown in Table 1.

TABLE 1

| Occurrence of C18 fatty acids in wild-type and transgenic cyanobacteria | | | | | | |
|---|---|---|---|---|---|---|
| SOURCE | 18:0 | 18:1 | 18:2 | γ18:3 | α18:3 | 18:4 |
| Anabaena (wild type) | + | + | + | − | + | − |
| Anabaena + ORF1(F) | + | + | + | − | + | − |
| Anabaena + ORF1(R) | + | + | + | − | + | − |
| Anabaena + ORF2(F) | + | + | + | + | + | + |
| Anabaena + ORF2(R) | + | + | + | − | + | − |
| Synechocystis (wild type) | + | + | + | + | − | − |

As assessed by GLC analysis, GLA deficient *Anabaena* gain the function of GLA production when the construct containing ORF2 in forward orientation is introduced by transconjugation. Transconjugants containing constructs with ORF2 in reverse orientation to the carboxylase promoter, or ORF1 in either orientation, show no GLA production. This analysis demonstrates that the single open reading frame (ORF2) within the 1884 bp fragment encodes Δ6-desaturase. The 1884 bp fragment is shown as SEQ ID NO:3. This is substantiated by the overall similarity of the hydropathy profiles between Δ6-desaturase and Δ12-desaturase [Wada et al. (1990) *Nature* 347] as shown in FIG. 1 as (A) and (B), respectively.

Isolated nucleic acids encoding Δ6-desaturase can be identified from other GLA-producing organisms by the gain of function analysis described above, or by nucleic acid hybridization techniques using the isolated nucleic acid which encodes *Anabaena* Δ6-desaturase as a hybridization probe. Both genomic and cDNA cloning methods are known to the skilled artisan and are contemplated by the present invention. The hybridization probe can comprise the entire DNA sequence disclosed as SEQ. ID NO:1, or a restriction fragment or other DNA fragment thereof, including an oligonucleotide probe. Methods for cloning homologous genes by cross-hybridization are known to the ordinarily skilled artisan and can be found, for example, in Sambrook (1989) and Beltz et al. (1983) *Methods in Enzymology* 100, 266.

Transgenic organisms which gain the function of GLA production by introduction of DNA encoding Δ-desaturase also gain the function of octadecatetraeonic acid (18:4 Δ$^{6,9,12,15}$) production. Octadecatetraeonic acid is present normally in fish oils and in some plant species of the Boraginaceae family (Craig et al. [1964] *J. Amer. Oil Chem. Soc.* 41, 209–211; Gross et al. [1976] *Can. J. Plant Sci.* 56, 659–664). In the transgenic organisms of the present invention, octadecatetraenoic acid results from further desaturation of α-linolenic acid by Δ6-desaturase or desaturation of GLA by Δ15-desaturase.

The 359 amino acids encoded by ORF2, i.e. the open reading frame encoding Δ6-desaturase, are shown as SEQ. ID NO:2. The present invention further contemplates other nucleotide sequences which encode the amino acids of SEQ ID NO:2. It is within the ken of the ordinarily skilled artisan to identify such sequences which result, for example, from the degeneracy of the genetic code. Furthermore, one of ordinary skill in the art can determine, by the gain of function analysis described hereinabove, smaller subfragments of the 1884 bp fragment containing ORF2 which encode Δ6-desaturase.

The present invention contemplates any such polypeptide fragment of Δ6-desaturase and the nucleic acids therefor which retain activity for converting LA to GLA.

In another aspect of the present invention, a vector containing the 1884 bp fragment or a smaller fragment containing the promoter, coding sequence and termination region of the Δ6-desaturase gene is transferred into an organism, for example, cyanobacteria, in which the Δ6-desaturase promoter and termination regions are functional. Accordingly, organisms producing recombinant Δ6-desaturase are provided by this invention. Yet another aspect of this invention provides isolated Δ6-desaturase, which can be purified from the recombinant organisms by standard methods of protein purification. (For example, see Ausubel et al. [1987] *Current Protocols in Molecular Biology*, Green Publishing Associates, New York).

Vectors containing DNA encoding Δ6-desaturase are also provided by the present invention. It will be apparent to one of ordinary skill in the art that appropriate vectors can be constructed to direct the expression of the Δ6-desaturase coding sequence in a variety of organisms. Replicable expression vectors are particularly preferred. Replicable expression vectors as described herein are DNA or RNA molecules engineered for controlled expression of a desired gene, i.e. the Δ6-desaturase gene. Preferably the vectors are plasmids, bacteriophages, cosmids or viruses. Shuttle vectors, e.g. as described by Wolk et al. (1984) *Proc. Natl. Acad. Sci. USA*, 1561–1565 and Bustos et al. (1991) *J. Bacteriol.* 174, 7525–7533, are also contemplated in accordance with the present invention. Sambrook et al. (1989), Goeddel, ed. (1990) *Methods in Enzymology* 185 Academic Press, and Perbal (1988) *A Practical Guide to Molecular Cloning*, John Wiley and Sons, Inc., provide detailed reviews of vectors into which a nucleic acid encoding the present Δ6-desaturase can be inserted and expressed. Such vectors also contain nucleic acid sequences which can effect expression of nucleic acids encoding Δ6-desaturase. Sequence elements capable of effecting expression of a gene product include promoters, enhancer elements, upstream activating sequences, transcription termination signals and polyadenylation sites. Both constitutive and tissue specific promoters are contemplated. For transformation of plant cells, the cauliflower mosaic virus (CaMV) 35S promoter and promoters which are regulated during plant seed maturation are of particular interest. All such promoter and transcriptional regulatory elements, singly or in combination, are contemplated for use in the present replicable expression vectors and are known to one of ordinary skill in the art. The CaMV 35S promoter is described, for example, by Restrepo et al. (1990) *Plant Cell* 2, 987. Genetically engineered and mutated regulatory sequences are also contemplated.

The ordinarily skilled artisan can determine vectors and regulatory elements suitable for expression in a particular host cell. For example, a vector comprising the promoter from the gene encoding the carboxylase of *Anabaena* operably linked to the coding region of Δ6-desaturase and further operably linked to a termination signal from *Synechocystis* is appropriate for expression of Δ6-desaturase in cyanobacteria. "Operably linked" in this context means that the promoter and terminator sequences effectively function to regulate transcription. As a further example, a vector appropriate for expression of Δ6-desaturase in transgenic plants can comprise a seed-specific promoter sequence derived from helianthinin, napin, or glycin operably linked to the Δ6-desaturase coding region and further operably linked to a seed termination signal or the nopaline synthase termination signal.

In particular, the helianthinin regulatory elements disclosed in applicant's copending U.S. patent application Ser. No. 682,354, filed Apr. 8, 1991 and incorporated herein by reference, are contemplated as promoter elements to direct the expression of the Δ6-desaturase of the present invention.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such hybrid vectors are well-known to those of ordinary skill in the art and can be found in references such as Sambrook et al. (1989), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in the hybrid vectors other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985) *Nature* 313, 358. Prokaryotic and eukaryotic signal sequences are disclosed, for example, by Michaelis et al. (1982) *Ann. Rev. Microbiol.* 36, 425.

A further aspect of the instant invention provides organisms other than cyanobacteria which contain the DNA encoding the Δ6-desaturase of the present invention. The transgenic organisms contemplated in accordance with the present invention include bacteria, cyanobacteria, fungi, and plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989).

A variety of plant transformation methods are known. The Δ6-desaturase gene can be introduced into plants by a leaf disk transformation-regeneration procedure as described by Horsch et al. (1985) *Science* 227, 1229. Other methods of transformation, such as protoplast culture (Horsch et al. (1984) *Science* 223, 496; DeBlock et al. (1984) *EMBO J.* 2, 2143; Barton et al. (1983) *Cell* 32, 1033) can also be used and are within the scope of this invention. In a preferred embodiment plants are transformed with *Agrobacterium*-derived vectors. However, other methods are available to insert the Δ6-desaturase gene of the present invention into plant cells. Such alternative methods include biolistic approaches (Klein et al. (1987) *Nature* 327, 70), electroporation, chemically-induced DNA uptake, and use of viruses or pollen as vectors.

When necessary for the transformation method, the Δ6-desaturase gene of the present invention can be inserted into a plant transformation vector, e.g. the binary vector described by Bevan (1984) *Nucleic Acids Res.* 12, 8111. Plant transformation vectors can be derived by modifying the natural gene transfer system of *Agrobacterium tumefa-*

*ciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

Surface-sterilized leaf disks are inoculated with the "disarmed" foreign DNA-containing *A. tumefaciens*, cultured for two days, and then transferred to antibiotic-containing medium. Transformed shoots are selected after rooting in medium containing the appropriate antibiotic, transferred to soil and regenerated.

Another aspect of the present invention provides transgenic plants or progeny of these plants containing the isolated DNA of the invention. Both monocotyledenous and dicotyledenous plants are contemplated. Plant cells are transformed with the isolated DNA encoding Δ6-desaturase by any of the plant transformation methods described above. The transformed plant cell, usually in a callus culture or leaf disk, is regenerated into a complete transgenic plant by methods well-known to one of ordinary skill in the art (e.g. Horsch et al. (1985) *Science* 227, 1129). In a preferred embodiment, the transgenic plant is sunflower, oil seed rape, maize, tobacco, peanut or soybean. Since progeny of transformed plants inherit the DNA encoding Δ6 -desaturase, seeds or cuttings from transformed plants are used to maintain the transgenic plant line.

The present invention further provides a method for providing transgenic plants with an increased content of GLA. This method includes introducing DNA encoding Δ6-desaturase into plant cells which lack or have low levels of GLA but contain LA, and regenerating plants with increased GLA content from the transgenic cells. In particular, commercially grown crop plants are contemplated as the transgenic organism, including, but not limited to, sunflower, soybean, oil seed rape, maize, peanut and tobacco.

The present invention further provides a method for providing transgenic organisms which contain GLA. This method comprises introducing DNA encoding Δ6 -desaturase into an organism which lacks or has low levels of GLA, but contains LA. In another embodiment, the method comprises introducing one or more expression vectors which comprise DNA encoding Δ12-desaturase and Δ6-desaturase into organisms which are deficient in both GLA and LA. Accordingly, organisms deficient in both LA and GLA are induced to produce LA by the expression of Δ12-desaturase, and GLA is then generated due to the expression of Δ6-desaturase. Expression vectors comprising DNA encoding Δ12-desaturase, or Δ12 -desaturase and Δ6-desaturase, can be constructed by methods of recombinant technology known to one of ordinary skill in the art (Sambrook et al., 1989) and the published sequence of Δ12-desaturase (Wada et al [1990] *Nature* (London) 347, 200–203. In addition, it has been discovered in accordance with the present invention that nucleotides 2002–3081 of SEQ. ID NO:1 encode cyanobacterial Δ12-desaturase. Accordingly, this sequence can be used to construct the subject expression vectors. In particular, commercially grown crop plants are contemplated as the transgenic organism, including, but not limited to, sunflower, soybean, oil seed rape, maize, peanut and tobacco.

The present invention is further directed to a method of inducing chilling tolerance in plants. Chilling sensitivity may be due to phase transition of lipids in cell membranes. Phase transition temperature depends upon the degree of unsaturation of fatty acids in membrane lipids, and thus increasing the degree of unsaturation, for example by introducing Δ6-desaturase to convert LA to GLA, can induce or improve chilling resistance. Accordingly, the present method comprises introducing DNA encoding Δ6-desaturase into a plant cell, and regenerating a plant with improved chilling resistance from said transformed plant cell. In a preferred embodiment, the plant is a sunflower, soybean, oil seed rape, maize, peanut or tobacco plant.

The following examples further illustrate the present invention.

EXAMPLE 1

Strains and Culture Conditions

*Synechocystis* (PCC 6803, ATCC 27184), *Anabaena* (PCC 7120, ATCC 27893) and *Synechococcus* (PCC 7942, ATCC 33912) were grown photoautotrophically at 30° C. in BG11N+ medium (Rippka et al. [1979] *J. Gen. Microbiol.* 111, 1–61) under illumination of incandescent lamps (60 $\mu E.m^{-2}.S^{-1}$). Cosmids and plasmids were selected and propagated in *Escherichia coli* strain DH5α on LB medium supplemented with antibiotics at standard concentrations as described by Maniatis et al. (1982) *Molecular Cloning: A Laboratory Manual*, Cold Spring Harbor Laboratory, Cold Spring, N.Y.

EXAMPLE 2

Construction of *Synechocystis* Cosmid Genomic Library

Total genomic DNA from *Synechocystis* (PCC 6803) was partially digested with Sau3A and fractionated on a sucrose gradient (Ausubel et al. [1987] *Current Protocols in Molecular Biology*, Greene Publishing Associates and Wiley Interscience, New York). Fractions containing 30 to 40 kb DNA fragments were selected and ligated into the dephosphorylated BamHI site of the cosmid vector, pDUCA7 (Buikema et al. [1991] *J. Bacteriol.* 173, 1879–1885). The ligated DNA was packaged in vitro as described by Ausubel et al. (1987), and packaged phage were propagated in *E. coli* DH5α containing the AvaI and Eco4711 methylase helper plasmid, pRL528 as described by Buikema et al. (1991). A total of 1152 colonies were isolated randomly and maintained individually in twelve 96-well microtiter plates.

EXAMPLE 3

Gain-of-Function Expression of GLA in *Anabaena*

*Anabaena* (PCC 7120), a filamentous cyanobacterium, is deficient in GLA but contains significant amounts of linoleic acid, the precursor for GLA (FIG. 2; Table 2). The *Synechocystis* cosmid library described in Example 2 was conjugated into *Anabaena* (PCC 7120) to identify transconjugants that produce GLA. *Anabaena* cells were grown to mid-log phase in BG11N+ liquid medium and resuspended in the same medium to a final concentration of approximately $2\times10^8$ cells per ml. A mid-log phase culture of *E. coli* RP4 (Burkardt et al. [1979] *J. Gen. Microbiol.* 114, 341–348) grown in LB containing ampicillin was washed and resuspended in fresh LB medium. *Anabaena* and RP4 were then mixed and spread evenly on BG11N+ plates containing 5% LB. The cosmid genomic library was replica plated onto LB plates containing 50 µg/ml kanamycin and 17.5 µg/ml chloramphenicol and was subsequently patched onto BG11N+ plates containing *Anabaena* and RP4. After 24 hours of incubation at 30° C., 30 µg/ml of neomycin was underlaid; and incubation at 30° C. was continued until transconjugants appeared.

Individual transconjugants were isolated after conjugation and grown in 2 ml BG11N+ liquid medium with 15 µg/ml neomycin. Fatty acid methyl esters were prepared from wild type cultures and cultures containing pools of ten transconjugants as follows. Wild type and transgenic cyanobacterial cultures were harvested by centrifugation and washed twice with distilled water. Fatty acid methyl esters were extracted from these cultures as described by Dahmer et al. (1989) *J. Amer. Oil. Chem. Soc.* 66, 543–548 and were analyzed by Gas Liquid Chromatography (GLC) using a Tracor-560 equipped with a hydrogen flame ionization detector and capillary column (30 m×0.25 mm bonded FSOT Superox II, Alltech Associates Inc., Ill.). Retention times and co-chromatography of standards (obtained from Sigma Chemical Co.) were used for identification of fatty acids. The average fatty acid composition was determined as the ratio of peak area of each C18 fatty acid normalized to an internal standard.

Representative GLC profiles are shown in FIG. 2. C18 fatty acid methyl esters are shown. Peaks were identified by comparing the elution times with known standards of fatty acid methyl esters and were confirmed by gas chromatography-mass spectrometry. Panel A depicts GLC analysis of fatty acids of wild type *Anabaena*. The arrow indicates the migration time of GLA. Panel B is a GLC profile of fatty acids of transconjugants of *Anabaena* with pAM542+1.8F. Two GLA producing pools (of 25 pools representing 250 transconjugants) were identified that produced GLA. Individual transconjugants of each GLA positive pool were analyzed for GLA production; two independent transconjugants, AS13 and AS75, one from each pool, were identified which expressed significant levels of GLA and which contained cosmids, cSy13 and csy75, respectively (FIG. 3). The cosmids overlap in a region approximately 7.5 kb in length. A 3.5 kb NheI fragment of csy75 was recloned in the vector pDUCA7 and transferred to *Anabaena* resulting in gain-of-function expression of GLA (Table 2).

Two NheI/Hind III subfragments (1.8 and 1.7 kb) of the 3.5 kb Nhe I fragment of csy75–3.5 were subcloned into "pBLUESCRIPT" (Stratagene) (FIG. 3) for sequencing. Standard molecular biology techniques were performed as described by Maniatis et al. (1982) and Ausubel et al. (1987). Dideoxy sequencing (Sanger et al. [1977] *Proc. Natl. Acad. Sci. USA* 74, 5463–5467) of pBS1.8 was performed with "SEQUENASE" (United States Biochemical) on both strands by using specific oligonucleotide primers synthesized by the Advanced DNA Technologies Laboratory (Biology Department, Texas A & M University). DNA sequence analysis was done with the GCG (Madison, Wis.) software as described by Devereux et al. (1984) *Nucleic Acids Res.* 12, 387–395.

Both NheI/HindIII subfragments were transferred into a conjugal expression vector, AM542, in both forward and reverse orientations with respect to a cyanobacterial carboxylase promoter and were introduced into *Anabaena* by conjugation. Transconjugants containing the 1.8 kb fragment in the forward orientation (AM542-1.8F) produced significant quantities of GLA and octadecatetraenoic acid (FIG. 2; Table 2). Transconjugants containing other constructs, either reverse oriented 1.8 kb fragment or forward and reverse oriented 1.7 kb fragment, did not produce detectable levels of GLA (Table 2).

FIG. 2 compares the C18 fatty acid profile of an extract from wild type *Anabaena* (FIG. 2A) with that of transgenic *Anabaena* containing the 1.8 kb fragment of csy75–3.5 in the forward orientation (FIG. 2B). GLC analysis of fatty acid methyl esters from AM542–1.8F revealed a peak with a retention time identical to that of authentic GLA standard. Analysis of this peak by gas chromatography-mass spectrometry (GC-MS) confirmed that it had the same mass fragmentation pattern as a GLA reference sample. Transgenic *Anabaena* with altered levels of polyunsaturated fatty acids were similar to wild type in growth rate and morphology.

TABLE 2

Composition of C18 Fatty Acids in Wild Type and Transgenic Cyanobacteria

| Strain | Fatty acid (%) | | | | | |
|---|---|---|---|---|---|---|
| | 18:0 | 18:1 | 18:2 | 18:3(α) | 18:3(γ) | 18:4 |
| Wild Type | | | | | | |
| Synechocystis (sp. PCC6803) | 13.6 | 4.5 | 54.5 | — | 27.3 | — |
| Anabaena (sp. PCC7120) | 2.9 | 24.8 | 37.1 | 35.2 | — | — |
| Synechococcus (sp. PCC7942) | 20.6 | 79.4 | — | — | — | — |
| Anabaena Transconjugants | | | | | | |
| cSy75 | 3.8 | 24.4 | 22.3 | 9.1 | 27.9 | 12.5 |
| cSy75-3.5 | 4.3 | 27.6 | 18.1 | 3.2 | 40.4 | 6.4 |
| pAM542 - 1.8F | 4.2 | 13.9 | 12.1 | 19.1 | 25.4 | 25.4 |
| pAM542 - 1.8R | 7.7 | 23.1 | 38.4 | 30.8 | — | — |
| pAM542 - 1.7F | 2.8 | 27.8 | 36.1 | 33.3 | — | — |
| pAM542 - 1.7R | 2.8 | 25.4 | 42.3 | 29.6 | — | — |
| Synechococcus Transformants | | | | | | |
| pAM854 | 27.8 | 72.2 | — | — | — | — |
| pAM854 - Δ$^{12}$ | 4.0 | 43.2 | 46.0 | — | — | — |
| pAM854 - Δ$^6$ | 18.2 | 81.8 | — | — | — | — |
| pAM854 - Δ$^6$ & Δ$^{12}$ | 42.7 | 25.3 | 19.5 | — | 16.5 | — |

18:0, stearic acid; 18:1, oleic acid; 18:2, linoleic acid; 18:3(α), α-linolenic acid; 18:3(γ), γ-linolenic acid; 18:4, octadecatetraenoic acid

EXAMPLE 4

Transformation of *Synechococcus* with Δ6 and Δ12 Desaturase Genes

A third cosmid, cSy7, which contains a Δ12-desaturase gene, was isolated by screening the *Synechocystis* genomic library with a oligonucleotide synthesized from the published *Synechocystis* Δ12-desaturase gene sequence (Wada et al. [1990] *Nature* (London) 347, 200–203). A 1.7 kb AvaI fragment from this cosmid containing the Δ12-desaturase gene was identified and used as a probe to demonstrate that cSy13 not only contains a Δ6-desaturase gene but also a Δ12-desaturase gene (FIG. 3). Genomic Southern blot analysis further showed that both the Δ6- and Δ12-desaturase genes are unique in the *Synechocystis* genome so that both functional genes involved in C18 fatty acid desaturation are linked closely in the *Synechocystis* genome.

The unicellular cyanobacterium *Synechococcus* (PCC 7942) is deficient in both linoleic acid and GLA(3). The Δ12 and Δ6-desaturase genes were cloned individually and together into pAM854 (Bustos et al. [1991] *J. Bacteriol.* 174, 7525–7533), a shuttle vector that contains sequences necessary for the integration of foreign DNA into the genome of *Synechococcus* (Golden et al. [1987] Methods in Enzymol. 153, 215–231). *Synechococcus* was transformed with these gene constructs and colonies were selected. Fatty acid methyl esters were extracted from transgenic *Synechococcus* and analyzed by GLC.

Table 2 shows that the principal fatty acids of wild type *Synechococcus* are stearic acid (18:0) and oleic acid (18:1). *Synechococcus* transformed with pAM854-Δ12 expressed linoleic acid (18:2) in addition to the principal fatty acids. Transformants with pAM854-Δ6 and Δ12 produced both linoleate and GLA (Table 1). These results indicated that *Synechococcus* containing both Δ12- and Δ6-desaturase genes has gained the capability of introducing a second double bond at the Δ12 position and a third double bond at the Δ6 position of C18 fatty acids. However, no changes in fatty acid composition was observed in the transformant containing pAM854-Δ6, indicating that in the absence of substrate synthesized by the Δ12 desaturase, the Δ6-desaturase is inactive. This experiment further confirms that the 1.8 kb NheI/HindIII fragment (FIG. 3) contains both coding and promoter regions of the *Synechocystis* Δ6-desaturase gene. Transgenic *Synechococcus* with altered levels of polyunsaturated fatty acids were similar to wild type in growth rate and morphology.

EXAMPLE 5

Nucleotide Sequence of Δ6-Desaturase

Figure 4B:
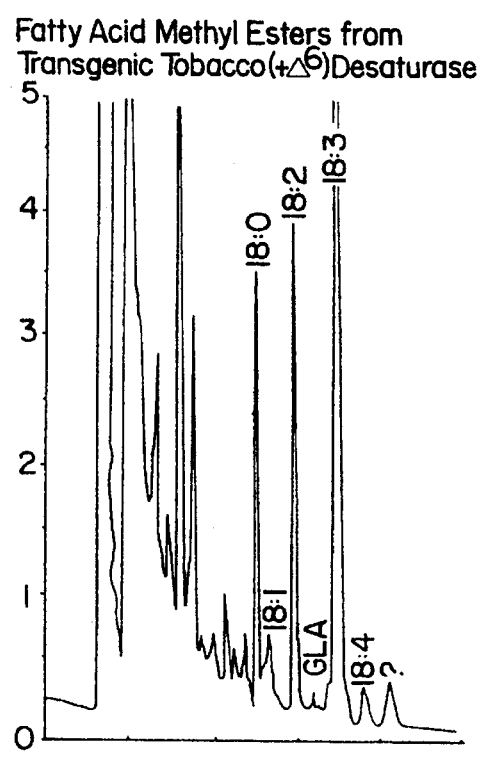

The nucleotide sequence of the 1.8 kb fragment of csy75-3.5 including the functional Δ6-desaturase gene was determined. An open reading frame encoding a polypeptide of 359 amino acids was identified (FIG. 4). A Kyte-Doolittle hydropathy analysis (Kyte et al. [1982] *J. Mol. Biol.* 157, 105–132) identified two regions of hydrophobic amino acids that could represent transmembrane domains (FIG. 1A); furthermore, the hydropathic profile of the Δ6-desaturase is similar to that of the Δ12-desaturase gene (FIG. 1B; Wada et al.) and Δ9-desaturases (Thiede et al. [1986] *J. Biol. Chem.* 261, 13230–13235). However, the sequence similarity between the *Synechocystis* Δ6- and Δ12-desaturases is less than 40% at the nucleotide level and approximately 18% at the amino acid level.

EXAMPLE 6

Transfer of Cyanobacterial Δ6-Desaturase into Tobacco

The cyanobacterial Δ6-desaturase gene was mobilized into a plant expression vector and transferred to tobacco using *Agrobacterium* mediated gene transfer techniques. To ensure that the transferred desaturase is appropriately expressed in leaves and developing seeds and that the desaturase gene product is targeted to the endoplasmic reticulum or the chloroplast, various expression cassettes with *Synechocystis* Δ-desaturase open reading frame (ORF) were constructed. Components of these cassettes include: (i) a 35S promoter or seed specific promoter derived from the sunflower helianthinin gene to drive Δ6-desaturase gene expression in all plant tissues or only in developing seeds respectively, (ii) a putative signal peptide either from carrot extensin gene or sunflower helianthinin gene to target newly synthesized Δ6-desaturase into the ER, (iii) an ER lumen retention signal sequence (KDEL) at the COOH-terminal of the Δ6-desaturase ORF, and (iv) an optimized transit peptide to target Δ6 desaturase into the chloroplast. The 35S promoter is a derivative of pRTL2 described by Restrepo et al. (1990). The optimized transit peptide sequence is described by Van de Broeck et al. (1985). The carrot extensin signal peptide is described by Chen et al. (1985) *EMBO J.* 9, 2145.

Transgenic tobacco plants were produced containing a chimeric cyanobacterial desaturase gene, comprised of the *Synechocystis* Δ6 desaturase gene fused to an endoplasmic reticulum retention sequence (KDEL) and extensin signal peptide driven by the CaMV 35S promoter. PCR amplifications of transgenic tobacco genomic DNA indicate that the Δ6 desaturase gene was incorporated into the tobacco genome. Fatty acid methyl esters of leaves of these transgenic tobacco plants were extracted and analyzed by Gas Liquid Chromatography (GLC). These transgenic tobacco accumulated significant amounts of GLA (FIG. 4). FIG. 4 shows fatty acid methyl esters as determined by GLC. Peaks were identified by comparing the elution times with known standards of fatty acid methyl ester. Accordingly, cyanobacterial genes involved in fatty acid metabolism can be used to generate transgenic plants with altered fatty acid compositions.

What is claimed:

1. An isolated nucleic acid encoding cyanobacterial Δ6-desaturase wherein said isolated nucleic acid is isolatable from a cyanobacteria that produces gamma linolenic acid.

2. An isolated nucleic acid having the sequence of SEQ ID NO:3.

3. An isolated nucleic acid encoding a *Synechocystis* Δ6-desaturase.

4. A vector comprising the nucleic acid of any one of claims 1–3.

5. An expression vector comprising the isolated nucleic acid of any one of claims 1–3 operably linked to a promoter capable of effecting expression of the gene product of said isolated nucleic acid.

6. An expression vector comprising the isolated nucleic acid of any one of claims 1–3 operably linked to a promoter and a termination signal capable of effecting expression of the gene product of said isolated nucleic acid.

7. The expression vector of claim 5 wherein said promoter is a Δ6-desaturase promoter, an *Anabaena* carboxylase promoter, a helianthinin promoter, a glycin promoter, a napin promoter, or a helianthinin tissue-specific promoter.

8. The expression vector of claim 6 wherein said promoter is a Δ6-desaturase promoter, an *Anabaena* carboxylase promoter, a helianthinin promoter, a glycin promoter, a napin promoter, or a helianthinin tissue-specific promoter.

9. The expression vector of claim 6 wherein said termination signal is a *Synechocystis* termination signal, a nopaline synthase termination signal, or a seed termination signal.

10. A bacterial or plant cell comprising the vector of claim 4.

11. A bacterial or plant cell comprising the vector of claim 5.

12. A bacterial or plant cell comprising the vector of claim 6.

13. A method of inducing production of gamma linolenic acid (GLA) in a bacteria deficient or lacking in GLA wherein said bacteria produces linoleic acid which comprises transforming said bacteria with the isolated nucleic acid of claim 1.

14. A method of inducing production of gamma linolenic acid (GLA) in a bacteria deficient or lacking in GLA wherein said bacteria produces linoleic acid which comprises transforming said bacteria with the vector of claim 4.

15. A method of inducing production of gamma linolenic acid (GLA) in a bacteria deficient or lacking in GLA wherein said bacteria produces linoleic acid which comprises transforming said bacteria with the vector of claim 5.

16. A method of inducing production of gamma linolenic acid (GLA) wherein said bacteria deficient of lacking in GLA wherein said bacteria produces linoleic acid which comprises transforming said bacteria with the vector of claim 6.

17. A method of inducing production of gamma linolenic acid (GLA) in a bacteria deficient or lacking in GLA and linoleic acid (LA) which comprises transforming said bacteria with an isolated nucleic acid encoding cyanobacterial Δ6-desaturase and an isolated nucleic acid encoding Δ12-desaturase.

18. A method of inducing production of gamma linolenic acid (GLA) in a bacteria deficient or lacking in GLA and linoleic acid (LA) which comprises transforming said bacteria with at least one expression vector comprising an isolated nucleic acid encoding cyanobacterial Δ6-desaturase and an isolated nucleic acid encoding Δ12-desaturase.

19. The method of any one of claims 17 or 18 wherein said isolated nucleic acid encoding Δ6-desaturase comprises nucleotides 2002 to 3081 of SEQ. ID. NO:1.

20. A method of inducing production of octadecatetraeonic acid in a bacteria deficient or lacking in gamma linolenic acid wherein said bacteria produces linoleic acid which comprises transforming said bacteria with the isolated nucleic acid of claim 1.

21. A method of inducing production of octadecatetraeonic acid in a bacteria deficient or lacking in gamma linolenic acid wherein said bacteria produces linoleic acid which comprises transforming said bacteria with vector of claim 4.

22. A method of inducing production of octadecatetraeonic acid in a bacteria deficient or lacking in gamma linolenic acid wherein said bacteria produces linoleic acid which comprises transforming said bacteria with vector of claim 5.

23. A method of inducing production of octadecatetraeonic acid in a bacteria deficient or lacking in gamma linolenic acid wherein said bacteria produces linoleic acid which comprises transforming said bacteria with vector of claim 6.

* * * * *

UNITED STATES PATENT AND TRADEMARK OFFICE
CERTIFICATE OF CORRECTION

PATENT NO. : 5,552,306
DATED : September 3, 1996
INVENTOR(S) : Terry Thomas, et al.

It is certified that error appears in the above-indentified patent and that said Letters Patent is hereby corrected as shown below:

Column 3, line 23: "GLAd-" should read --GLA- --

Column 3, line 28: "wellknown" should read --well-known--

Column 9, lines 43, 45 & 49: "csy75" should read --cSy75--

Column 10, line 8: "csy75" should read --cSy75--

Column 11, line 36: "csy75" should read --cSy75--

Column 22, line 22, Claim 16: delete "wherein said" and insert --in a--

Signed and Sealed this

Fifth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 3588 base pairs
      ( B ) TYPE: nucleic acid
      ( C ) STRANDEDNESS: both
      ( D ) TOPOLOGY: linear ( i i ) MOLECULE TYPE: DNA (genomic)

( i x ) FEATURE:
      ( A ) NAME/KEY: CDS
      ( B ) LOCATION: 2002..3081

( x i ) SEQUENCE DESCRIPTION: SEQ ID NO:1:

| | | | | | |
|---|---|---|---|---|---|
| GCTAGCCACC | AGTGACGATG | CCTTGAATTT | GGCCATTCTG | ACCCAGGCCC | GTATTCTGAA | 60 |
| TCCCCGCATT | CGCATTGTTA | ATCGTTTGTT | CAACCATGCC | CTGGGTAAAC | GTTAGACAC | 120 |
| CACCTTGCCA | GACCACGTTA | GTTGAGTGT | TTCCGCCCTG | GCGGCCCCGA | TTTTTCCTT | 180 |
| TGCGGCTTTG | GGCAATCAGG | CGATCGGGCA | ATTGCGTTTG | TTTGACCAGA | CTTGGCCCAT | 240 |
| TCAGGAAATT | GTCATCACC | AAGACCATCC | CTGGCTCAAT | TTACCCCTGG | CGGATTTATG | 300 |
| GGATGATCCG | AGCCGAATGT | TGATCTATTA | CCTACCGGCC | CACAGTGAAA | CGGATTTAGT | 360 |
| AGGCGCAGTG | GTGAATAATT | TAACGTTGCA | ATCTGGGGAC | CATTTAATAG | TGGGACAAAA | 420 |
| ACCCCAACCC | AAGACCAAAC | GGCGATCGCC | TTGGCGCAAA | TTTTCCAAAC | TGATTACCAA | 480 |
| CCTGCGGGAG | TATCAGCGGT | ATGTCCAACA | GGTGATATGG | GTGGTGTTGT | TTTTATTGTT | 540 |
| GATGATTTTT | CTGGCCACCT | TCATCTACGT | TTCCATTGAT | CAACATATTG | CCCCAGTGGA | 600 |
| CGCGTTGTAT | TTTTCCGTGG | GCATGATTAC | CGGGGCCGGT | GGCAAGGAAG | AGGTGGCCGA | 660 |
| AAAGTCCCCC | GATATCATCA | AGTATTCAC | AGTGGTGATG | ATGATCGCCG | GGCGGGGGT | 720 |
| GATTGGTATT | TGTTATGCCC | TACTGAATGA | TTTCATCCTT | GGCAGTCGCT | TTAGTCAGTT | 780 |
| TTTGGATGCG | GCCAAGTTAC | CCGATCGCCA | TCACATCATC | ATTTGTGGGC | TGGGGGGAGT | 840 |
| GAGCATGGCC | ATTATTGAAG | AGTTAATTCA | CCAGGGCCAT | GAAATTGTGG | TAATCGAAAA | 900 |
| GGATACAGAT | AATCGTTTCT | TGCATACGGC | CCGCTCCCTG | GGGGTGCCCG | TAATTGTGGA | 960 |
| GGATGCCCGC | CTAGAAAGAA | CGTTGGCCTG | CGCCAATATC | AACCGAGCCG | AAGCCATTGT | 1020 |
| GGTGGCCACC | AGCGACGACA | CCGTTAACTT | GGAAATTGGC | CTAACTGCCA | AGGCGATCGC | 1080 |
| CCCTAGCCTG | CCAGTGGTGT | TGCGTTGCCA | GGATGCCCAG | TTTAGCCTGT | CCCTGCAGGA | 1140 |
| AGTATTTGAA | TTTGAAACGG | TGCTTTGTCC | GGCGGAATTG | GCCACCTATT | CCTTTGCGGC | 1200 |
| GGCGGCCCTG | GGGGGCAAAA | TTTGGGCAA | CGGCATGACC | GATGATTTGC | TGTGGGTAGC | 1260 |
| CCTAGCCACC | TTAATCACTC | CTAACCATCC | CTTTGCCGAC | CAATTGGTTA | AAATTGCAGC | 1320 |
| CCAAAAGTCT | GATTTCGTTC | CCCTCTATCT | AGAACGGGGT | GGCAAAACCA | TCCATAGCTG | 1380 |
| GGAATTATTG | GGTACCCATC | TCGACTCTGG | AGACGTGTTG | TATTTAACCA | TGCCCGCCAC | 1440 |
| TGCCCTAGAG | CAACTTTGGC | GATCGCCCCG | TGCCACTGCT | GATCCTCTGG | ACTCTTTTTT | 1500 |
| GGTTTAGCAT | GGGGGGATGG | AACTCTTGAC | TCGGCCCAAT | GGTGATCAAG | AAAGAACGCT | 1560 |
| TTGTCTATGT | TTAGTATTTT | TAAGTTAACC | AACAGCAGAG | GATAACTTCC | AAAAGAAATT | 1620 |
| AAGCTCAAAA | AGTAGCAAAA | TAAGTTTAAT | TCATAACTGA | GTTTTACTGC | TAAACAGCGG | 1680 |
| TGCAAAAAAG | TCAGATAAAA | TAAAAGCTTC | ACTTCGGTTT | TATATTGTGA | CCATGGTTCC | 1740 |
| CAGGCATCTG | CTCTAGGGAG | TTTTTCCGCT | GCCTTTAGAG | AGTATTTTCT | CCAAGTCGGC | 1800 |
| TAACTCCCCC | ATTTTTAGGC | AAAATCATAT | ACAGACTATC | CCAATATTGC | CAGAGCTTTG | 1860 |
| ATGACTCACT | GTAGAAGGCA | GACTAAAATT | CTAGCAATGG | ACTCCCAGTT | GGAATAAATT | 1920 |
| TTTAGTCTCC | CCCGGCGCTG | GAGTTTTTTT | GTAGTTAATG | GCGGTATAAT | GTGAAAGTTT | 1980 |
| TTTATCTATT | TAAATTTATA | A ATG CTA | ACA GCG GAA | AGA ATT AAA | TTT ACC | 2031 |
| | | Met Leu<br>1 | Thr Ala Glu<br>5 | Arg Ile Lys | Phe Thr<br>10 | |
| CAG AAA CGG | GGG TTT CGT | CGG GTA CTA | AAC CAA CGG | GTG GAT GCC | TAC | 2079 |
| Gln Lys Arg<br>15 | Gly Phe Arg | Arg Val Leu<br>20 | Asn Gln Arg | Val Asp Ala<br>25 | Tyr | |
| TTT GCC GAG | CAT GGC CTG | ACC CAA AGG | GAT AAT CCC | TCC ATG TAT | CTG | 2127 |
| Phe Ala Glu<br>30 | His Gly Leu | Thr Gln Arg<br>35 | Asp Asn Pro | Ser Met Tyr<br>40 | Leu | |

| | | | | | | | | | | | | | | | | |
|---|---|---|---|---|---|---|---|---|---|---|---|---|---|---|---|---|
| AAA | ACC | CTG | ATT | ATT | GTG | CTC | TGG | TTG | TTT | TCC | GCT | TGG | GCC | TTT | GTG | 2175 |
| Lys | Thr | Leu | Ile | Ile | Val | Leu | Trp | Leu | Phe | Ser | Ala | Trp | Ala | Phe | Val | |
| | | | 45 | | | | 50 | | | | 55 | | | | | |
| CTT | TTT | GCT | CCA | GTT | ATT | TTT | CCG | GTG | CGC | CTA | CTG | GGT | TGT | ATG | GTT | 2223 |
| Leu | Phe | Ala | Pro | Val | Ile | Phe | Pro | Val | Arg | Leu | Leu | Gly | Cys | Met | Val | |
| | 60 | | | | 65 | | | | | 70 | | | | | | |
| TTG | GCG | ATC | GCC | TTG | GCG | GCC | TTT | TCC | TTC | AAT | GTC | GGC | CAC | GAT | GCC | 2271 |
| Leu | Ala | Ile | Ala | Leu | Ala | Ala | Phe | Ser | Phe | Asn | Val | Gly | His | Asp | Ala | |
| 75 | | | | 80 | | | | | 85 | | | | | 90 | | |
| AAC | CAC | AAT | GCC | TAT | TCC | TCC | AAT | CCC | CAC | ATC | AAC | CGG | GTT | CTG | GGC | 2319 |
| Asn | His | Asn | Ala | Tyr | Ser | Ser | Asn | Pro | His | Ile | Asn | Arg | Val | Leu | Gly | |
| | | | | 95 | | | | | 100 | | | | | 105 | | |
| ATG | ACC | TAC | GAT | TTT | GTC | GGG | TTA | TCT | AGT | TTT | CTT | TGG | CGC | TAT | CGC | 2367 |
| Met | Thr | Tyr | Asp | Phe | Val | Gly | Leu | Ser | Ser | Phe | Leu | Trp | Arg | Tyr | Arg | |
| | | | 110 | | | | | 115 | | | | | 120 | | | |
| CAC | AAC | TAT | TTG | CAC | CAC | ACC | TAC | ACC | AAT | ATT | CTT | GGC | CAT | GAC | GTG | 2415 |
| His | Asn | Tyr | Leu | His | His | Thr | Tyr | Thr | Asn | Ile | Leu | Gly | His | Asp | Val | |
| | | 125 | | | | | 130 | | | | | 135 | | | | |
| GAA | ATC | CAT | GGA | GAT | GGC | GCA | GTA | CGT | ATG | AGT | CCT | GAA | CAA | GAA | CAT | 2463 |
| Glu | Ile | His | Gly | Asp | Gly | Ala | Val | Arg | Met | Ser | Pro | Glu | Gln | Glu | His | |
| | 140 | | | | 145 | | | | | 150 | | | | | | |
| GTT | GGT | ATT | TAT | CGT | TTC | CAG | CAA | TTT | TAT | ATT | TGG | GGT | TTA | TAT | CTT | 2511 |
| Val | Gly | Ile | Tyr | Arg | Phe | Gln | Gln | Phe | Tyr | Ile | Trp | Gly | Leu | Tyr | Leu | |
| 155 | | | | | 160 | | | | | 165 | | | | | 170 | |
| TTC | ATT | CCC | TTT | TAT | TGG | TTT | CTC | TAC | GAT | GTC | TAC | CTA | GTG | CTT | AAT | 2559 |
| Phe | Ile | Pro | Phe | Tyr | Trp | Phe | Leu | Tyr | Asp | Val | Tyr | Leu | Val | Leu | Asn | |
| | | | | 175 | | | | | 180 | | | | | 185 | | |
| AAA | GGC | AAA | TAT | CAC | GAC | CAT | AAA | ATT | CCT | CCT | TTC | CAG | CCC | CTA | GAA | 2607 |
| Lys | Gly | Lys | Tyr | His | Asp | His | Lys | Ile | Pro | Pro | Phe | Gln | Pro | Leu | Glu | |
| | | | 190 | | | | | 195 | | | | | 200 | | | |
| TTA | GCT | AGT | TTG | CTA | GGG | ATT | AAG | CTA | TTA | TGG | CTC | GGC | TAC | GTT | TTC | 2655 |
| Leu | Ala | Ser | Leu | Leu | Gly | Ile | Lys | Leu | Leu | Trp | Leu | Gly | Tyr | Val | Phe | |
| | | 205 | | | | | 210 | | | | | 215 | | | | |
| GGC | TTA | CCT | CTG | GCT | CTG | GGC | TTT | TCC | ATT | CCT | GAA | GTA | TTA | ATT | GGT | 2703 |
| Gly | Leu | Pro | Leu | Ala | Leu | Gly | Phe | Ser | Ile | Pro | Glu | Val | Leu | Ile | Gly | |
| | 220 | | | | 225 | | | | | 230 | | | | | | |
| GCT | TCG | GTA | ACC | TAT | ATG | ACC | TAT | GGC | ATC | GTG | GTT | TGC | ACC | ATC | TTT | 2751 |
| Ala | Ser | Val | Thr | Tyr | Met | Thr | Tyr | Gly | Ile | Val | Val | Cys | Thr | Ile | Phe | |
| 235 | | | | | 240 | | | | | 245 | | | | | 250 | |
| ATG | CTG | GCC | CAT | GTG | TTG | GAA | TCA | ACT | GAA | TTT | CTC | ACC | CCC | GAT | GGT | 2799 |
| Met | Leu | Ala | His | Val | Leu | Glu | Ser | Thr | Glu | Phe | Leu | Thr | Pro | Asp | Gly | |
| | | | | 255 | | | | | 260 | | | | | 265 | | |
| GAA | TCC | GGT | GCC | ATT | GAT | GAC | GAG | TGG | GCT | ATT | TGC | CAA | ATT | CGT | ACC | 2847 |
| Glu | Ser | Gly | Ala | Ile | Asp | Asp | Glu | Trp | Ala | Ile | Cys | Gln | Ile | Arg | Thr | |
| | | | 270 | | | | | 275 | | | | | 280 | | | |
| ACG | GCC | AAT | TTT | GCC | ACC | AAT | AAT | CCC | TTT | TGG | AAC | TGG | TTT | TGT | GGC | 2895 |
| Thr | Ala | Asn | Phe | Ala | Thr | Asn | Asn | Pro | Phe | Trp | Asn | Trp | Phe | Cys | Gly | |
| | | 285 | | | | | 290 | | | | | 295 | | | | |
| GGT | TTA | AAT | CAC | CAA | GTT | ACC | CAC | CAT | CTT | TTC | CCC | AAT | ATT | TGT | CAT | 2943 |
| Gly | Leu | Asn | His | Gln | Val | Thr | His | His | Leu | Phe | Pro | Asn | Ile | Cys | His | |
| | 300 | | | | 305 | | | | | 310 | | | | | | |
| ATT | CAC | TAT | CCC | CAA | TTG | GAA | AAT | ATT | ATT | AAG | GAT | GTT | TGC | CAA | GAG | 2991 |
| Ile | His | Tyr | Pro | Gln | Leu | Glu | Asn | Ile | Ile | Lys | Asp | Val | Cys | Gln | Glu | |
| 315 | | | | 320 | | | | | 325 | | | | | 330 | | |
| TTT | GGT | GTG | GAA | TAT | AAA | GTT | TAT | CCC | ACC | TTC | AAA | GCG | GCG | ATC | GCC | 3039 |
| Phe | Gly | Val | Glu | Tyr | Lys | Val | Tyr | Pro | Thr | Phe | Lys | Ala | Ala | Ile | Ala | |
| | | | | 335 | | | | 340 | | | | | 345 | | | |
| TCT | AAC | TAT | CGC | TGG | CTA | GAG | GCC | ATG | GGC | AAA | GCA | TCG | TGACATTGCC | | | 3088 |
| Ser | Asn | Tyr | Arg | Trp | Leu | Glu | Ala | Met | Gly | Lys | Ala | Ser | | | | |
| | | | 350 | | | | | 355 | | | | 360 | | | | |

-continued

```
TTGGGATTGA AGCAAAATGG CAAAATCCCT CGTAAATCTA TGATCGAAGC CTTTCTGTTG    3148

CCCGCCGACC AAATCCCCGA TGCTGACCAA AGGTTGATGT TGGCATTGCT CCAAACCCAC    3208

TTTGAGGGGG TTCATTGGCC GCAGTTTCAA GCTGACCTAG GAGGCAAAGA TTGGGTGATT    3268

TTGCTCAAAT CCGCTGGGAT ATTGAAAGGC TTCACCACCT TTGGTTTCTA CCCTGCTCAA    3328

TGGGAAGGAC AAACCGTCAG AATTGTTTAT TCTGGTGACA CCATCACCGA CCCATCCATG    3388

TGGTCTAACC CAGCCCTGGC CAAGGCTTGG ACCAAGGCCA TGCAAATTCT CCACGAGGCT    3448

AGGCCAGAAA AATTATATTG GCTCCTGATT TCTTCCGGCT ATCGCACCTA CCGATTTTTG    3508

AGCATTTTTG CCAAGGAATT CTATCCCCAC TATCTCCATC CCACTCCCCC GCCTGTACAA    3568

AATTTTATCC ATCAGCTAGC                                                3588
```

( 2 ) INFORMATION FOR SEQ ID NO:2:

( i ) SEQUENCE CHARACTERISTICS:
    ( A ) LENGTH: 359 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Leu Thr Ala Glu Arg Ile Lys Phe Thr Gln Lys Arg Gly Phe Arg
 1               5                  10                  15

Arg Val Leu Asn Gln Arg Val Asp Ala Tyr Phe Ala Glu His Gly Leu
                20                  25                  30

Thr Gln Arg Asp Asn Pro Ser Met Tyr Leu Lys Thr Leu Ile Ile Val
            35                  40                  45

Leu Trp Leu Phe Ser Ala Trp Ala Phe Val Leu Phe Ala Pro Val Ile
        50                  55                  60

Phe Pro Val Arg Leu Leu Gly Cys Met Val Leu Ala Ile Ala Leu Ala
 65                  70                  75                  80

Ala Phe Ser Phe Asn Val Gly His Asp Ala Asn His Asn Ala Tyr Ser
                85                  90                  95

Ser Asn Pro His Ile Asn Arg Val Leu Gly Met Thr Tyr Asp Phe Val
               100                 105                 110

Gly Leu Ser Ser Phe Leu Trp Arg Tyr Arg His Asn Tyr Leu His His
            115                 120                 125

Thr Tyr Thr Asn Ile Leu Gly His Asp Val Glu Ile His Gly Asp Gly
        130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
                165                 170                 175

Phe Leu Tyr Asp Val Tyr Leu Val Leu Asn Lys Gly Lys Tyr His Asp
            180                 185                 190

His Lys Ile Pro Pro Phe Gln Pro Leu Glu Leu Ala Ser Leu Leu Gly
        195                 200                 205

Ile Lys Leu Leu Trp Leu Gly Tyr Val Phe Gly Leu Pro Leu Ala Leu
    210                 215                 220

Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
```

|     |     |     |     |     | 260 |     |     |     |     | 265 |     |     |     |     | 270 |     |     |
| --- | --- | --- | --- | --- | --- | --- | --- | --- | --- | --- | --- | --- | --- | --- | --- | --- | --- |
| Asp | Glu | Trp 275 | Ala | Ile | Cys | Gln | Ile 280 | Arg | Thr | Thr | Ala | Asn 285 | Phe | Ala | Thr |
| Asn | Asn 290 | Pro | Phe | Trp | Asn | Trp 295 | Phe | Cys | Gly | Gly | Leu 300 | Asn | His | Gln | Val |
| Thr 305 | His | His | Leu | Phe | Pro 310 | Asn | Ile | Cys | His | Ile 315 | His | Tyr | Pro | Gln | Leu 320 |
| Glu | Asn | Ile | Ile | Lys 325 | Asp | Val | Cys | Gln | Glu 330 | Phe | Gly | Val | Glu | Tyr 335 | Lys |
| Val | Tyr | Pro | Thr 340 | Phe | Lys | Ala | Ala | Ile 345 | Ala | Ser | Asn | Tyr | Arg 350 | Trp | Leu |
| Glu | Ala | Met 355 | Gly | Lys | Ala | Ser |

( 2 ) INFORMATION FOR SEQ ID NO:3:

( i ) SEQUENCE CHARACTERISTICS:
        ( A ) LENGTH: 1884 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

```
AGCTTCACTT CGGTTTTATA TTGTGACCAT GGTTCCCAGG CATCTGCTCT AGGGAGTTTT      60
TCCGCTGCCT TTAGAGAGTA TTTTCTCCAA GTCGGCTAAC TCCCCCATTT TTAGGCAAAA     120
TCATATACAG ACTATCCCAA TATTGCCAGA GCTTGATGA CTCACTGTAG AAGGCAGACT      180
AAAATTCTAG CAATGGACTC CCAGTTGGAA TAAATTTTA GTCTCCCCCG GCGCTGGAGT      240
TTTTTTGTAG TTAATGGCGG TATAATGTGA AAGTTTTTA TCTATTTAAA TTTATAAATG      300
CTAACAGCGG AAAGAATTAA ATTTACCCAG AAACGGGGGT TTCGTCGGGT ACTAAACCAA     360
CGGGTGGATG CCTACTTTGC CGAGCATGGC CTGACCCAAA GGGATAATCC CTCCATGTAT     420
CTGAAAACCC TGATTATTGT GCTCTGGTTG TTTTCCGCTT GGGCCTTTGT GCTTTTTGCT     480
CCAGTTATTT TTCCGGTGCG CCTACTGGGT TGTATGGTTT GGCGATCGC CTTGGCGGCC     540
TTTTCCTTCA ATGTCGGCCA CGATGCCAAC CACAATGCCT ATTCCTCCAA TCCCCACATC     600
AACCGGGTTC TGGGCATGAC CTACGATTTT GTCGGGTTAT CTAGTTTTCT TTGGCGCTAT     660
CGCCACAACT ATTTGCACCA CACCTACACC AATATTCTTG GCCATGACGT GGAAATCCAT     720
GGAGATGGCG CAGTACGTAT GAGTCCTGAA CAAGAACATG TTGGTATTTA TCGTTTCCAG     780
CAATTTTATA TTTGGGGTTT ATATCTTTTC ATTCCCTTTT ATTGGTTTCT CTACGATGTC     840
TACCTAGTGC TTAATAAAGG CAAATATCAC GACCATAAAA TTCCTCCTTT CCAGCCCCTA     900
GAATTAGCTA GTTTGCTAGG GATTAAGCTA TTATGGCTCG GCTACGTTTT CGGCTTACCT     960
CTGGCTCTGG GCTTTTCCAT TCCTGAAGTA TTAATTGGTG CTTCGGTAAC CTATATGACC    1020
TATGGCATCG TGGTTTGCAC CATCTTTATG CTGGCCCATG TGTTGAATC AACTGAATTT    1080
CTCACCCCCG ATGGTGAATC CGGTGCCATT GATGACGAGT GGGCTATTTG CCAAATTCGT    1140
ACCACGGCCA ATTTTGCCAC CAATAATCCC TTTTGGAACT GGTTTTGTGG CGGTTTAAAT    1200
CACCAAGTTA CCCACCATCT TTTCCCCAAT ATTTGTCATA TTCACTATCC CAATTGGAA    1260
AATATTATTA AGGATGTTTG CCAAGAGTTT GGTGTGGAAT ATAAAGTTTA TCCCACCTTC    1320
AAAGCGGCGA TCGCCTCTAA CTATCGCTGG CTAGAGGCCA TGGGCAAAGC ATCGTGACAT    1380
TGCCTTGGGA TTGAAGCAAA ATGGCAAAAT CCCTCGTAAA TCTATGATCG AAGCCTTTCT    1440
```

| | | | | | | |
|---|---|---|---|---|---|---|
| GTTGCCCGCC | GACCAAATCC | CCGATGCTGA | CCAAAGGTTG | ATGTTGGCAT | TGCTCCAAAC | 1500 |
| CCACTTTGAG | GGGGTTCATT | GGCCGCAGTT | TCAAGCTGAC | CTAGGAGGCA | AAGATTGGGT | 1560 |
| GATTTTGCTC | AAATCCGCTG | GGATATTGAA | AGGCTTCACC | ACCTTTGGTT | TCTACCCTGC | 1620 |
| TCAATGGGAA | GGACAAACCG | TCAGAATTGT | TTATTCTGGT | GACACCATCA | CCGACCCATC | 1680 |
| CATGTGGTCT | AACCCAGCCC | TGGCCAAGGC | TTGGACCAAG | GCCATGCAAA | TTCTCCACGA | 1740 |
| GGCTAGGCCA | GAAAAATTAT | ATTGGCTCCT | GATTTCTTCC | GGCTATCGCA | CCTACCGATT | 1800 |
| TTTGAGCATT | TTTGCCAAGG | AATTCTATCC | CCACTATCTC | CATCCACTC | CCCCGCCTGT | 1860 |
| ACAAAATTTT | ATCCATCAGC | TAGC | | | | 1884 |